US011000630B2

(12) United States Patent
Detamore et al.

(10) Patent No.: US 11,000,630 B2
(45) Date of Patent: May 11, 2021

(54) HYDROGEL PRECURSORS HAVING NANOPARTICLES

(71) Applicant: THE UNIVERSITY OF KANSAS, Lawrence, KS (US)

(72) Inventors: Michael Detamore, Lawrence, KS (US); Emily Beck, Lawrence, KS (US); Stevin Gehrke, Lawrence, KS (US); Cory Berkland, Lawrence, KS (US)

(73) Assignee: THE UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 16/428,534

(22) Filed: May 31, 2019

(65) Prior Publication Data
US 2019/0314554 A1    Oct. 17, 2019

Related U.S. Application Data

(60) Division of application No. 14/918,229, filed on Oct. 20, 2015, now Pat. No. 10,335,515, which is a continuation-in-part of application No. PCT/US2014/057498, filed on Sep. 25, 2014.

(60) Provisional application No. 62/066,164, filed on Oct. 20, 2014, provisional application No. 61/882,397, filed on Sep. 25, 2013.

(51) Int. Cl.
| *A61L 27/48* | (2006.01) |
| *A61L 27/20* | (2006.01) |
| *A61L 27/38* | (2006.01) |
| *A61L 27/54* | (2006.01) |
| *A61L 27/52* | (2006.01) |
| *A61L 27/50* | (2006.01) |

(52) U.S. Cl.
CPC .............. *A61L 27/48* (2013.01); *A61L 27/20* (2013.01); *A61L 27/383* (2013.01); *A61L 27/3817* (2013.01); *A61L 27/3834* (2013.01); *A61L 27/50* (2013.01); *A61L 27/52* (2013.01); *A61L 27/54* (2013.01); *A61L 2430/06* (2013.01); *A61L 2430/32* (2013.01)

(58) Field of Classification Search
CPC .... A61L 27/48; A61L 27/3817; A61L 27/383; A61L 27/50; A61L 27/20; A61L 27/3834; A61L 27/54; A61L 27/52; A61L 2430/32; A61L 2430/06
See application file for complete search history.

(56) References Cited

U.S. PATENT DOCUMENTS

| 4,656,137 | A  | 4/1987  | Balassa |
| 8,017,155 | B2 | 9/2011  | Schwendeman et al. |
| 8,221,500 | B2 | 10/2012 | Truncale et al. |
| 8,277,832 | B2 | 10/2012 | Detamore et al. |
| 2008/0069857 | A1 | 3/2008 | Yeo et al. |
| 2009/0118423 | A1 | 5/2009 | Kumar et al. |
| 2011/0070271 | A1 | 3/2011 | Truncale et al. |
| 2011/0195107 | A1 | 8/2011 | Min et al. |
| 2011/0212894 | A1 | 9/2011 | Athanasiou et al. |

FOREIGN PATENT DOCUMENTS

| CN | 101890184 B    | 7/2013  |
| WO | 2012142569 A2  | 10/2012 |
| WO | 2013109959 A1  | 7/2013  |
| WO | 2014039012 A1  | 3/2014  |
| WO | 2015048317 A1  | 4/2015  |

OTHER PUBLICATIONS

International Search Report and Written Opinion of the International Searching Authority PCT/US2014/057498, dated Sep. 25, 2014.
Kwon, JS et al. Injectable Extracellular Matrix Hydrogel Developed Using Porcine Articular Cartilage, International Journal of Pharmaceutics, Sep. 15, 2013, vol. 454, No. 1, abstract pp. 184-185.

*Primary Examiner* — Matthew P Coughlin
*Assistant Examiner* — Thurman Wheeler
(74) *Attorney, Agent, or Firm* — Maschoff Brennan; Jonathan M. Benns

(57) ABSTRACT

An implantable hydrogel precursor composition can include: a cross-linkable polymer matrix that is biocompatible; and a plurality of polymer particles in the cross-linkable polymer matrix. The cross-linkable polymer matrix can include a cross-linkable hyaluronic acid polymer that has cross-linkable functional groups. The hyaluronic acid polymer can be a methacrylated hyaluronic acid polymer. The methacrylated hyaluronic acid polymer can have a molecular weight from about 500 kDa to about 1.8 MDa. The polymer particles can include a cross-linked hyaluronic acid. The cross-linkable polymer matrix having the polymer particles has a yield stress. The cross-linkable polymer matrix having the polymer particles has shape retention at physiological temperatures. The composition can include live cells in the cross-linkable polymer matrix. The composition can include a biologically active agent in the cross-linkable polymer matrix.

19 Claims, 6 Drawing Sheets

HYDROGEL PRECURSORS HAVING NANOPARTICLES

CROSS-REFERENCE

This patent application is a divisional application of U.S. patent application Ser. No. 14/918,229 filed Oct. 20, 2015, which claims priority to U.S. Provisional Application No. 62/066,164 filed Oct. 20, 2014; and U.S. patent application Ser. No. 14/918,229 filed Oct. 20, 2015 is a continuation-in-part of PCT application PCT/US2014/057498 filed Sep. 25, 2014, which claims priority to U.S. Provisional Application No. 61/882,397 filed Sep. 25, 2013, which applications are incorporated herein by specific reference in their entirety.

GOVERNMENT RIGHTS

This invention was made with government support under NSF0064451 and DMR0847759 awarded by the National Science Foundation and under R01 DE022472 and S10 RR024664 awarded by the National Institutes of Health. The government has certain rights in the invention.

BACKGROUND

Effective tissue engineering has the potential to improve the quality of life of millions of patients, and may even day or prevent future medical costs related to tissue regenerative procedures. Advances in tissue engineering for cartilage and bone are especially needed. Scaffolds possessing the functional and mechanical features resembling tissue, such as cartilage and bone, can be useful for tissue regeneration and useful for quality of life during tissue regeneration because this allows the scaffold to function as the tissue. Such scaffolds can be important in joints that are moved often and that support a lot of weight, such as knee joints; however, any cartilage or bone defect can benefit from a scaffold that has sufficient mechanical integrity to provide normal use functionality. The scaffolds for tissue engineering may be created to have suitable mechanical compression, shear stress resistance, and hydrostatic pressure SUMMARY In one embodiment, an implantable hydrogel precursor composition can include: a cross-linkable polymer matrix that is biocompatible; and a plurality of polymer particles in the cross-linkable polymer matrix. In one aspect, the cross-linkable polymer matrix includes a cross-linkable hyaluronic acid polymer that has cross-linkable functional groups. In one aspect, the hyaluronic acid polymer is a methacrylated hyaluronic acid polymer. In one aspect, the methacrylated hyaluronic acid polymer has a molecular weight from about 500 kDa to about 1.8 MDa. In one aspect, the polymer particles include a cross-linked hyaluronic acid. In one aspect, the polymer particles have a molecular weight of about 10 kDa to about 20 kDa. In one aspect, the polymer particles have a particle size of about 10 nm to about 500 nm. In one aspect, the cross-linkable polymer is present from about 2% to about 10% and the polymer particles are present from about 5% to about 30%. In one aspect, the ratio of cross-linkable polymer to polymer particles is from 1:15 to about 2:1. In one aspect, the cross-linkable polymer matrix having the polymer particles has a yield stress. In one aspect, the cross-linkable polymer matrix having the polymer particles has shape retention at physiological temperatures. In one aspect, the composition includes live cells in the cross-linkable polymer matrix. In one aspect, the composition includes a biologically active agent in the cross-linkable polymer matrix.

In one embodiment, a hydrogel composition can include: a crosslinked polymeric hydrogel matrix that is biocompatible; and a plurality of polymer particles in the crosslinked polymer matrix. In one aspect, the crosslinked polymeric hydrogel matrix is cross-linked methacrylated hyaluronic acid polymer and the polymer particle is cross-linked hyaluronic acid, wherein the crosslinked polymer matrix encapsulates the polymer particles. The hydrogel may also include features and components derived from the hydrogel precursor from which it was crosslinked from.

In one embodiment, a method of forming an implant can include: providing an implantable hydrogel precursor composition in accordance with the embodiments described herein; and crosslinking the cross-linkable polymer matrix to form a hydrogel containing the plurality of polymer particles. In one aspect, the method further includes shaping the hydrogel precursor composition while in the body. In one aspect, the method further includes: placing the hydrogel precursor in a defect in a tissue in the body; and crosslinking the cross-linkable polymer in the defect. In one aspect, the defect is in a cartilage tissue, and the method regenerates cartilage tissue. In one aspect, the defect is in a nerve tissue, and the method regenerates cartilage tissue. The tissue being regenerated with the hydrogel described herein can include cells, bioactive agents, growth factors, or other substances to facilitate the tissue regeneration.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1A:
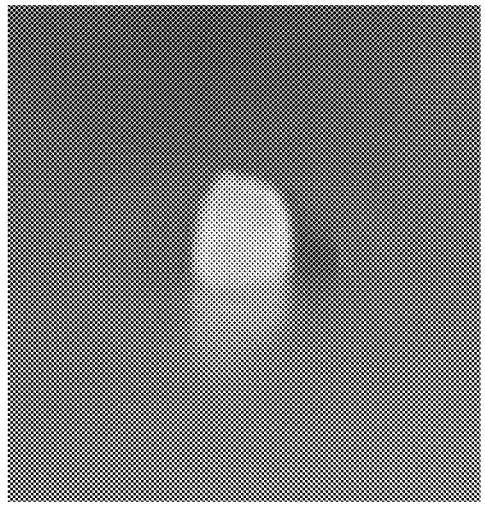
FIG. 1A includes an image of a gelatinous hydrogel precursor having 4% MeHA and 15% HAnp with shape retention.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to hydrogel compositions, hydrogel precursor compositions that are used to make hydrogels, and methods of making and using these compositions. The hydrogels can be used for tissue regeneration, and can be placed in a defect and molded to the shape of the defect. Also, the hydrogel precursors can be used for tissue regeneration, and can be loaded into a defect and then processed into the hydrogel while in the defect without leaking during placement or hydrogelation. In part, this is because the hydrogel precursor composition has shape retention characteristics and is not a liquid that will leak and flow out of a defect. While in the defect, the hydrogel precursor can stay within the defect during hydrogelation so as to mold to the shape of the defect. The hydrogel precursor can include particles in a matrix that has resistance to flowing. This allows the hydrogel precursor to have a paste-like or gel-like non-flowability instead of a flowable fluid behavior that is common in typical liquid hydrogel precursor solutions. The hydrogel precursor includes the particles in the matrix to have some interaction that associates the particles in the matrix to achieve a paste-like hydrogel precursor composition. In one example, the paste-like hydrogel precursor can include polymeric particles in a non-crosslinked or partially crosslinked (e.g., not fully crosslinked) polymer matrix, where the particles and matrix have some shape-retention characteristics that resist flowing as a fluid. In one example, the hydrogel precursor can include hyaluronic acid particles (e.g., nanoparticles or microparticles) with a crosslinkable hyaluronic acid polymer that can be crosslinked into a hyaluronic acid hydrogel that includes the hyaluronic acid particles.

The hydrogel precursor can have a yield stress and recovery that is superior to the matrix lacking the polymeric particles or having linear versions of the polymer particles (e.g., liner polymer). The polymer matrix having the polymeric nanoparticles exhibited a yield stress, demonstrating that the nanoparticles provide a paste-like property to the matrix, where the linear form (e.g., non-particulate) of polymer (e.g., hyaluronic acid) did not achieve a paste-like behavior in the matrix.

The hydrogel precursor having the paste-like property can be loaded into a mold or defect in a body and then crosslinked to retain the shape of the mold or defect. The hydrogel precursor may be shaped with a spatula or other instrument that can change the distribution or location of the matrix by spreading the matrix. The hydrogel precursor or formed hydrogel may also be shaped by cutting, such as with a sculpting tool, laser, knife, or the like. The hydrogel precursor can be photo-crosslinked or crosslinked by any suitable means. The hydrogel having the particles was characterized as a solid, where it was demonstrated that the inclusion of nanoparticles did not adversely affect the compressive modulus and that encapsulated bone marrow-derived mesenchymal stem cells remained viable in the hydrogel. The hydrogel precursor provides a system that exhibits a yield stress prior to crosslinking, and that can be crosslinked into a hydrogel that is capable of encapsulating cells that remain viable.

The crosslinked hydrogel having the particles can be used as a tissue regenerative material, such as a tissue engineering scaffold that can be implanted as a hydrogel precursor with or without cells therein. The resulting hydrogel can have high water content, moldable 3D structure, tunable mechanical properties, and ability to be delivered in a minimally invasive manner. The hydrogel precursor may be considered to be a colloidal gel that can be characterized as a mechanically dynamic paste-like material that can be molded into place (e.g., in defect) and will set (e.g., cured or hydrogelation) after placement (e.g., implantation).

The hydrogel precursor can attain cohesiveness through disruptable particle interactions, and can fill tissue defects, deliver bioactive signals, and promote new tissue formation in non-load bearing or load-bearing defect applications. The hydrogel precursor with shear-thinning rheological behavior can be made out of hyaluronic acid (HA) nanoparticles in a HA matrix. The HA-based hydrogel precursor has the ability to fully recover after compression to high strains. The HA-based hydrogel precursor also can recover after physically destroying and reassembling the composition, which may be attractive for applications such as for cartilage regeneration. This allows the hydrogel precursor to be broken into pieces and then recombined into the hydrogel precursor.

After hydrogelation, the composition is a crosslinked HA hydrogel having the HA particles, which forms a hydrogel suitable for load-bearing applications. The HA hydrogel can be used as a tissue engineering scaffold.

To achieve the hydrogel precursor and hydrogel scaffold, the HA nanoparticles (HAnp) are fabricated with a specific molecular weight (MW) that is within a suitable range and designed to achieve paste-like rheological behavior and a yield stress in the HA polymer matrix of the hydrogel precursor. The MW of the HAnp can range from about 5 kDa to about 50 kDa, from about 10 kDa to about 20 kDa, or from about 13 kDa to about 16 kDa, where the lowest MW can be 5 kDa and the highest MW can be 50 kDa, and a preferred MW can be 15 kDa. The particle size of the HAnp can range from about 10 nm to about 500 nm, from about 100 nm to about 300, or from about 225 nm to about 275 nm, where the lowest particle size can be 10 nm and the highest particle size can be 500, and a preferred particle size can be 246. The HA polymer of the HA polymer matrix of the hydrogel precursor can have a MW that can range from about 250 kDa to about 2.0 MDa, from about 500 kDa to about 1.8 MDa, or from about 900 kDa to about 1.2 MDa, where the lowest MW can be 250 KDa and the highest MW can be 2.0 MDa, and a preferred MW can be 750 KDa. The percent of the hydrogel precursor that is HAnp can range can range from about 5% to about 30%, from about 10% to about 20%, or from about 12% to about 17%, where the lowest percent can be 5% and the highest percent can be 30%, and a preferred percent can be 15%. The percent of the hydrogel precursor that is the HA polymer can range can range from about 1% to about 20%, from about 2% to about 10%, or from about 3% to about 5%, where the lowest percent can be 1% and the highest percent can be 20%, and a preferred percent can be 4%.

When the HAnp are substituted with other polymeric nanoparticles, these other nanoparticles can have similar molecular weights and percentages. When the HA matrix polymers are substituted with other cross-linkable polymers, these other nanoparticles can have similar molecular weights and percentages. While the molecular weight of the other polymers (e.g., not HA) in the polymer matrix and polymer particles can vary, the hydrogel precursor should have the rheological properties described herein. As such, the molecular weights and percentages of the matrix polymers and particles may vary.

The hydrogel precursor may also include drugs, growth factors, peptides or extracellular matrix molecules in the matrix with the particles.

The hydrogel precursor may also include cells in the matrix with the particles. Examples of cells to include in the hydrogel precursor include adult connective tissue cells (e.g., chondrocytes), neural cells (e.g., neural stem cells), adult stem cells (e.g., bone marrow-derived mesenchymal stem cells, adipose-derived stem cells), induced pluripotent stem cells, and embryonic stem cells.

The nanoparticles can provide the yield stress to the polymer matrix of the hydrogel precursor that is especially desirable to enable a surgeon to mold the hydrogel precursor material into the defect site without the concern that the hydrogel precursor material will flow or leak from the defect, which is the main concern for traditional hydrogel precursor solutions. The HAnp can allow the surgeon to mold the hydrogel precursor composition to obtain appropriate contouring of the defect site, which in some cases may not be possible with traditional hydrogel precursor solutions that are flowable liquids. Therefore, combining these HAnp with a crosslinkable HA matrix allows the hydrogel precursor material to be implanted in situ with appropriate placement and contouring, and the hydrogel precursor can then be crosslinked to form a more rigid hydrogel structure. It was found that the hydrogel precursor having the HAnp in the HA matrix does not negatively influence the mechanics or cyto-compatibility of the hydrogel after crosslinking.

In one embodiment, the present technology includes preparing hydrogel precursors having nanoparticles and having paste-like rheological behavior prior to crosslinking into a hydrogel. The hydrogel precursor is a material that exhibits a yield stress prior to crosslinking, can recover its network rapidly upon deformation or destruction or yielding, and can then be crosslinked into a more rigid hydrogel that is capable of bearing loads and encapsulating cells that remain viable. In one example, the cross-linkable polymer may be a photo-crosslinkable polymers, such as methacrylated hyaluronic acid, and the polymer particles can be hyaluronic acid. The molecular weight of the photocrosslinkable polymer (MeHA) can be 1 MDa at 4% concentration. However, the molecular weight range of MeHA can be 500 kDa up to 1.8 MDa at a concentration of 0.5-10%. The molecular weight of the polymer particle (HAnp) can be 1.6 kDa. The concentration of HAnp is preferably 15%, but could be 10% up to 30% depending on the application. The percent of the methacrylation of the MeHA polymer can range can range from about 5% to about 40%, from about 20% to about 30%, or from about 23% to about 26%, where the lowest percent can be 5% and the highest percent can be 40%, and a preferred percent can be 25%. The HA nanoparticles can be mixed into a composition with a photocrosslinkable MeHA polymer matrix in order to allow for crosslinking with the HA nanoparticles into a HA hydrogel.

In a use example, the hydrogel precursor and hydrogel having the nanoparticles can be used to treat cartilage defects or bone defects. The hydrogel precursor and hydrogel can be used in any application where a paste-like hydrogel precursor material is desirable over a low-viscosity hydrogel precursor solution. Additionally, the hydrogel precursor and hydrogel can be used for nerve regeneration, where the injectable paste-like hydrogel precursor can be implanted and then crosslinked into a hydrogel in order to deliver cells and/or materials and/or bioactive signals to the spinal cord. These hydrogel precursor pastes can also be used for plastic surgery reconstruction. Moreover, the hydrogel precursor and hydrogel holds significant impact for any application of a hydrogel where a paste-like behavior is desired prior to crosslinking, including but not limited to healthcare applications. For example, applications that cannot tolerate a liquid draining away from an irregularly shaped defect, or spilling from any kind of container at an angle to the direction of gravity may benefit from the paste-like rheology of the hydrogel precursor that enables placement of the material prior to crosslinking.

In one example, the particles and/or photocrosslinkable polymer can include decellularized cartilage (DCC). Such DCC particles or crosslinkable polymer can be used in addition to the polymeric particles and crosslinkable matrix described herein, where the polymers are synthetic or non-natural. Accordingly, DCC particles or crosslinkable polymer can be used to supplement the HA particles and/or HA crosslinkable polymer. However, in any composition having such DCC particles or crosslinkable polymer, the composition also has the non-DCC particles and non-DCC crosslinkable polymer.

In one example, the particles and/or photocrosslinkable polymer of the hydrogel precursor described herein may be devoid of decellularized cartilage (DCC). Such DCC particles or crosslinkable polymer can be specifically omitted from the polymeric particles and crosslinkable matrix described herein. Accordingly, DCC particles or crosslinkable polymer may be excluded from the hydrogel precursor that has the HA particles and/or HA crosslinkable polymer.

In one embodiment, the hydrogel precursor and hydrogel compositions can include bioactive peptides, growth factors, drugs, bioactive agents, extracellular matrix, other biomaterials, and the like.

The polymeric nanoparticles in the cross-linkable polymer matrix of the hydrogel precursor can be any nanoparticles. In one option the nanoparticles can be a linear polymer that is balled into a particle. Otherwise, the nanoparticles can be a crosslinked particle. Any nanoparticle may provide the desired paste composition. The polymer for cross-linking can be any known hydrogel polymer. As such, the particle may be make of any hydrogel polymer that is formed into a nanoparticle with the high molecular weight and concentration described herein. The polymer particles described herein may be supplemented with other types of polymers formed as polymer particles. Also, non-polymeric particles may be included.

In one embodiment, a hydrogel precursor composition can include a crosslinkable polymer having high yield stress prior to crosslinking that can recover its network rapidly, and can then be crosslinked into a more rigid hydrogel that is capable of bearing loads and encapsulating viable cells. The hydrogel precursor also includes a polymer particle in a matrix formed by the crosslinkable polymer. In one aspect, the crosslinkable polymer prior to crosslinking is 1 MDa at about 4% concentration. In one aspect, the crosslinkable polymer the molecular weight can range from 500 kDa to 1.8 MDa at a concentration of 0.5-10%. In one aspect, the polymer particle has a concentration of about 15%, but can range from about 10% to about 30%. This allows the polymer particle to be present up to about 30%. The hydrogel precursor composition can be varied so as to obtain a paste-like composition that can be molded and sculptured to retain shape in a mold or defect prior to and during crosslinking into a hydrogel.

In one embodiment, a composition includes a hydrogel formed by crosslinking the crosslinkable polymer so as to contain the polymer particles in the crosslinked hydrogel.

In one embodiment, a method of tissue regeneration can include preparing a hydrogel precursor composition having a crosslinkable polymer containing a polymer particle. The method can include introducing the hydrogel precursor composition into a body, and crosslinking the crosslinkable polymer so as to contain the polymer particles therein and form a hydrogel. The tissue can be cartilage, bone, or nerve sheath, or other.

Figure 1B:
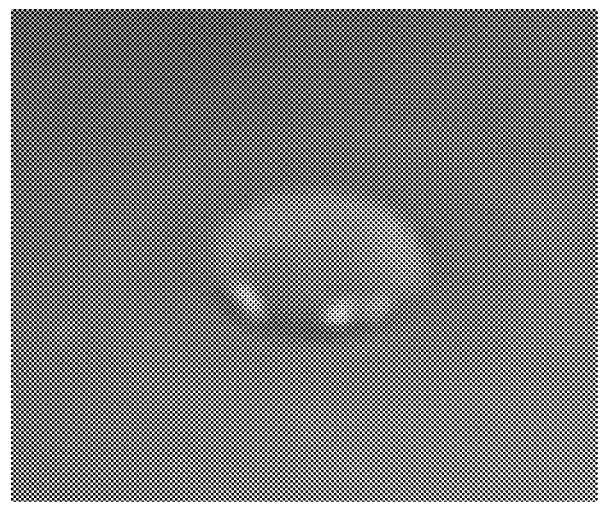
FIG. 1B includes an image of a liquid without shape retention formed by 4% MeHA and 15% HAlin (linear HA) and being a low viscosity liquid.
Figure 1C:
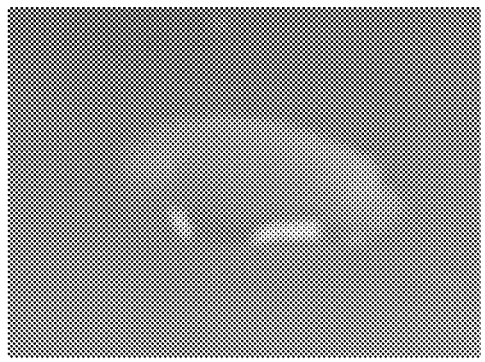
FIG. 1C includes an image of a liquid without shape retention formed by 4% MeHA and being a low viscosity liquid.

It was found that when HAnp (e.g., average diameter=246 nm) were mixed with MeHA (e.g., degree of methacrylation=21%), non-Newtonian paste-like behavior with shape-retention were observed as shown in FIGS. 1A-1C. In contrast, solutions composed of pure MeHA or MeHA solutions containing HAlin (e.g., linear HA) did not exhibit this behavior, and instead exhibited Newtonian or zero yield stress pseudoplastic behavior. STEM images of HAnp confirmed the formation of nanoparticles (see FIG. 1D).

Figure 1D:
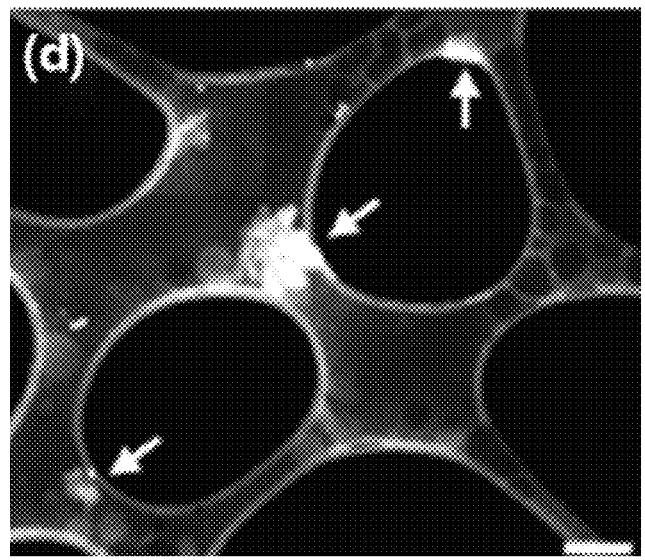
FIG. 1D includes a scanning transmission electron microscopy (STEM) of HAnp particles where the scale bar is 200 nm with the arrows showing individual HAnp particles.

FIG. 1A includes an image of a gelatinous hydrogel precursor having 4% MeHA and 15% HAnp with shape retention. FIG. 1B includes an image of a liquid without shape retention formed by 4% MeHA and 15% HAlin (linear HA) and being a low viscosity liquid. FIG. 1C includes an image of a liquid without shape retention formed by 4% MeHA and being a low viscosity liquid. FIG. 1D includes a scanning transmission electron microscopy (STEM) of HAnp particles where the scale bar is 200 nm with the arrows showing individual HAnps.

Figure 2A:
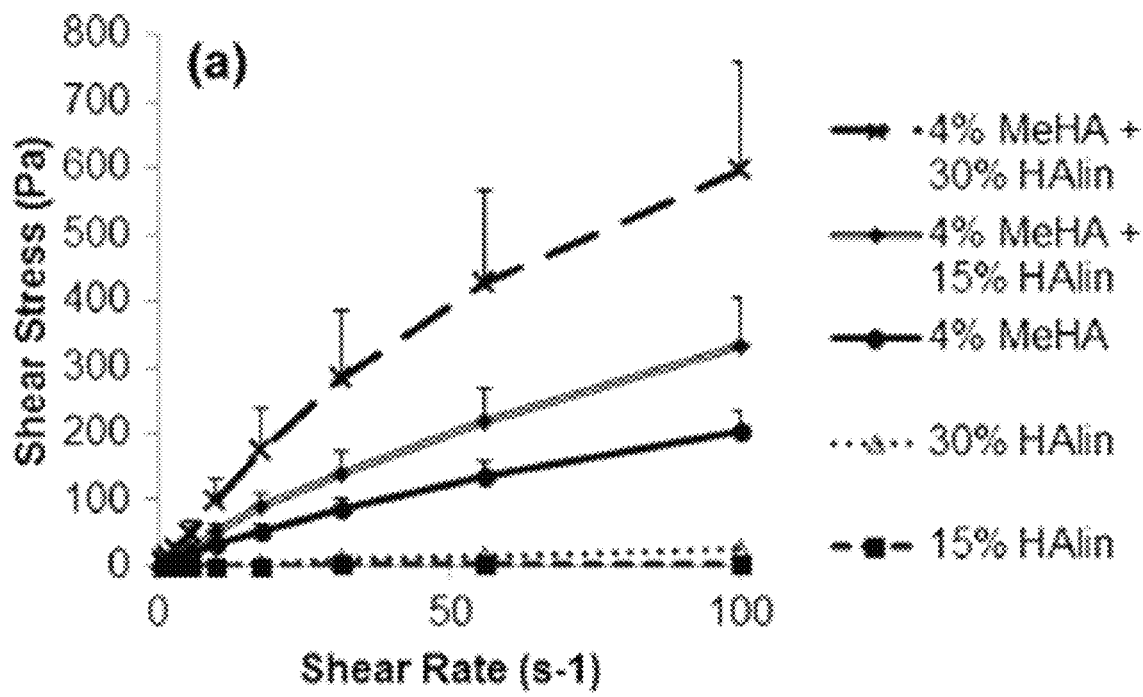
FIGS. 2A-2B include graphs that show the shear stress (Pa) versus shear rate ($S^{-1}$) for different compositions.
Figure 2B:
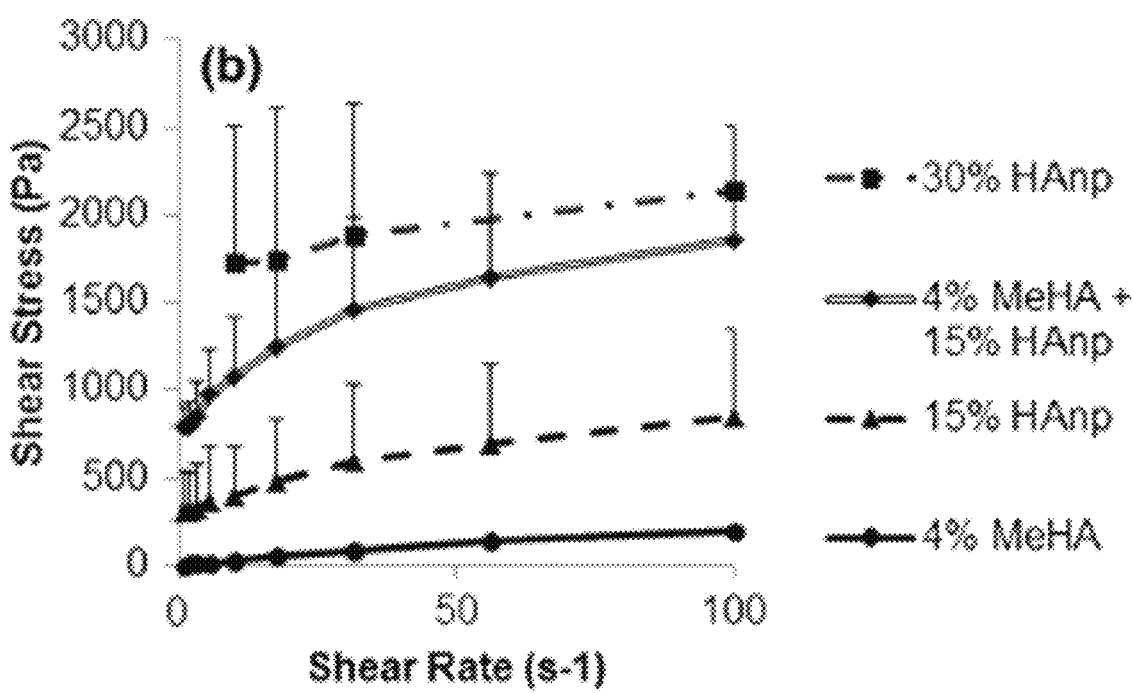
Figure 2C:
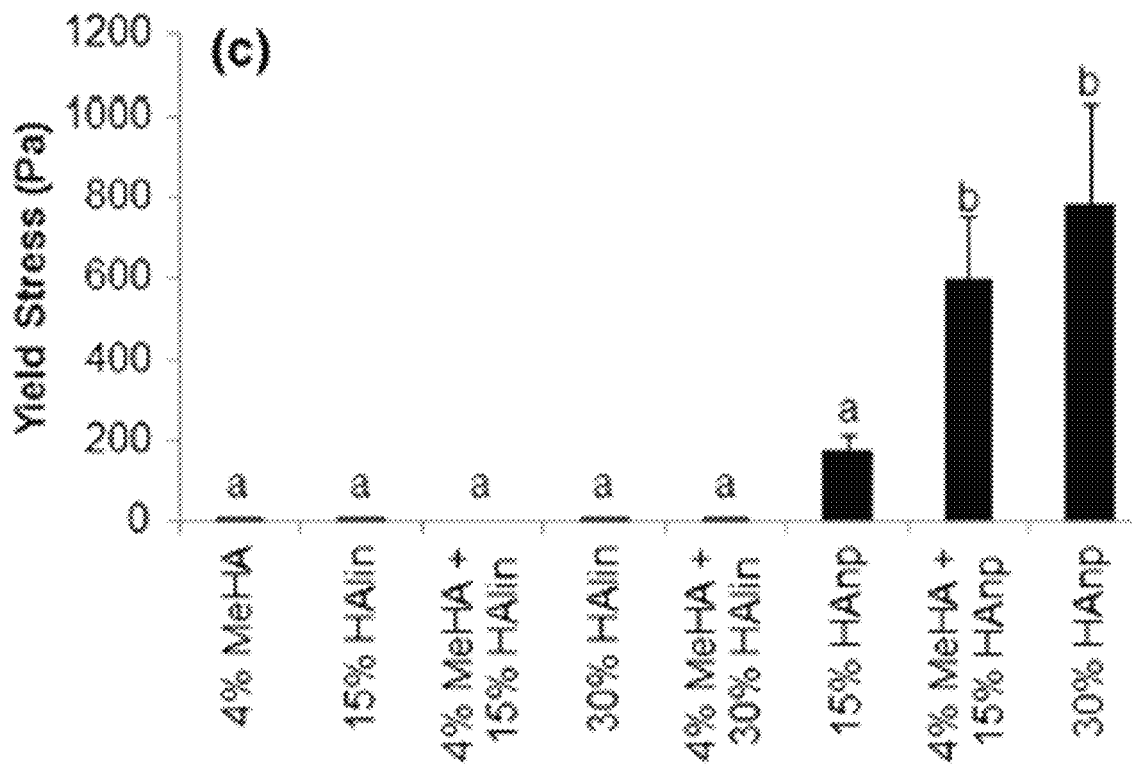
FIG. 2C includes a graph that shows the yield stress (Pa) fit to the Herschel-Bulkley equation for different compositions.
Figure 2D:
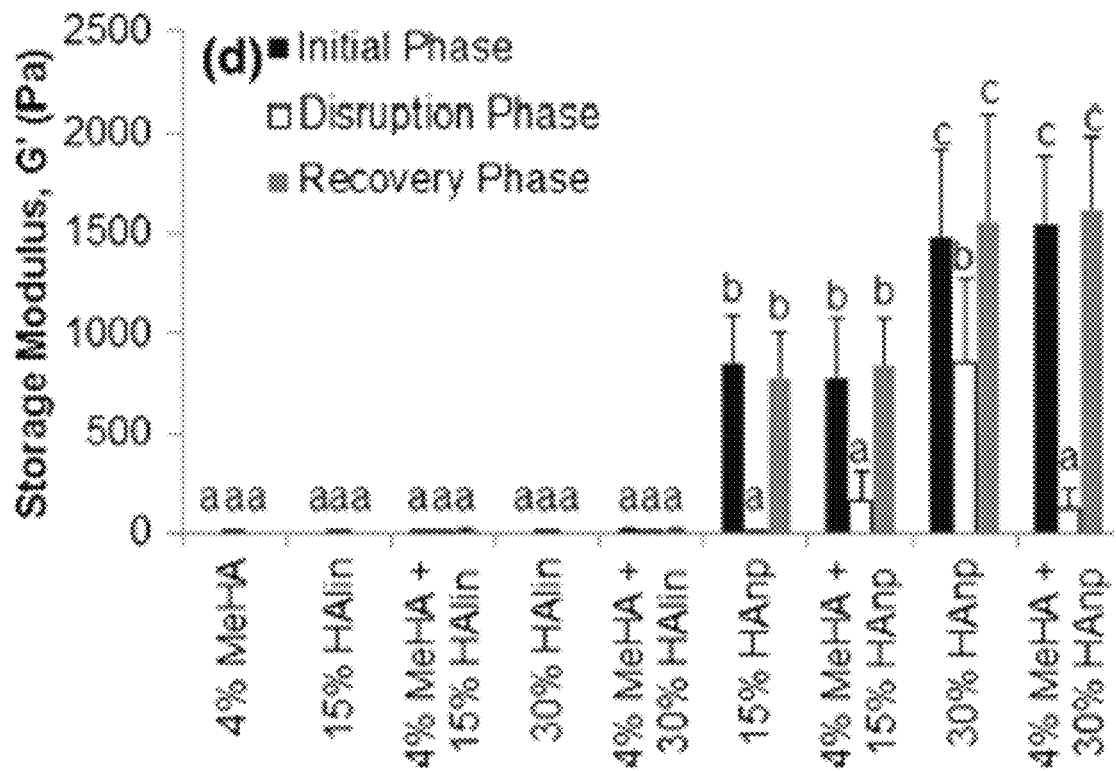
FIG. 2D includes a graph that shows the storage modulus at an initial phase, disruption phase, and recovery phase for different compositions.

FIGS. 2A-2B include graphs that show the shear stress (Pa) versus shear rate ($S^{-1}$) for different compositions. FIG. 2C includes a graph that shows the yield stress (Pa) fit to the Herschel-Bulkley equation (Equation 1; Eq. 1) for different compositions. The data shows that HAnp contributed to higher shear stress. Compositions containing HAnp were the only ones that exhibited a yield stress (see FIGS. 2A-2C). Solutions that contained unreacted HAlin polymer instead of HAnp did not exhibit a yield stress even though they were also fit to Eq. (1). The combination of 4% MeHA with 15% HAnp produced a synergistic effect, increasing the yield stress of the HAnp by a factor of 3.4 with the addition of the MeHA, which is surprising and unexpected. FIG. 2D includes a graph that shows the storage modulus at an initial phase, disruption phase, and recovery phase for different compositions, which shows that the hydrogel precursors having the nanoparticles are superior. The storage modulus of solutions lacking HAnp was negligible (e.g., all storage moduli were less than 20 Pa), but the storage modulus increased with increasing HAnp concentration (see FIG. 2D). Specifically, compared to the storage modulus of 4% MeHA, the storage moduli of 4% MeHA and HAnp increased 380-fold and 770-fold with the addition of either 15% HAnp or 30% HAnp, respectively. Recovery was assessed by the restoring of the original storage modulus after the disruption phase. All samples containing HAnp recovered their original storage moduli within 5 min of disruption.

Accordingly, the hydrogel precursor can have a shear stress of about 500 Pa to about 1000 Pa at a shear rate of about 1 $S^{-1}$, or from about 534.5 Pa to about 933.9 Pa at that shear rate, or from about 600 Pa to about 800 Pa at that shear rate, or a maximum shear stress of 1000 Pa or a minimum shear stress of 500 Pa, or preferred shear stress of 750 Pa at that shear rate. In another aspect, the hydrogel precursor can have a shear stress of about 550 Pa to about 960 PA at a shear rate of 1.78 $S^{-1}$, or from about 573 Pa to about 956 Pa at that shear rate, or from about 650 Pa to about 800 Pa at that shear rate, or a maximum shear stress of 960 Pa or a minimum shear stress of 550 Pa, or preferred shear stress of 750 Pa at that shear rate. In another aspect, the hydrogel precursor can have a shear stress of about 900 Pa to about 1300 Pa at a shear rate of 5.6 $S^{-1}$, or from about 921 Pa to about 1221 Pa at that shear rate, or from about 950 Pa to about 1100 Pa at that shear rate, or a maximum shear stress of 1300 Pa or a minimum shear stress of 900 Pa, or preferred shear stress of 1100 Pa at that shear rate.

In one embodiment, the hydrogel precursor can have a yield stress of about 400 Pa to about 800 Pa, or from about 459 Pa to about 788 Pa, or from about 500 Pa to about 600 Pa, or a maximum yield stress of 800 Pa, or a minimum yield stress of 400 Pa, or preferred yield stress of 575 Pa.

In one embodiment, the hydrogel precursor can have a storage modulus at the initial phase of about 400 Pa to about 1100 Pa, or from about 449 Pa to about 1085 Pa, or from about 500 Pa to about 800 Pa, or a maximum storage modulus of 100 Pa or a minimum storage modulus of 400, or preferred storage modulus of 777 Pa. In one embodiment, the hydrogel precursor can have a storage modulus at the disruption phase of about 10 Pa to about 400 Pa, or from about 28 Pa to about 338 Pa, or from about 100 Pa to about 200 Pa, or a maximum storage modulus of 400 or a minimum storage modulus of 10 Pa, or preferred storage modulus of 160 Pa. In one embodiment, the hydrogel precursor can have a storage modulus at the recovery phase of about 500 Pa to about 1200 Pa, or from about 550 Pa to about 1152 Pa, or from about 700 Pa to about 1p000 Pa, or a maximum storage modulus of 1200 or a minimum storage modulus of 500 Pa, or preferred storage modulus of 839 Pa.

Figure 3A:
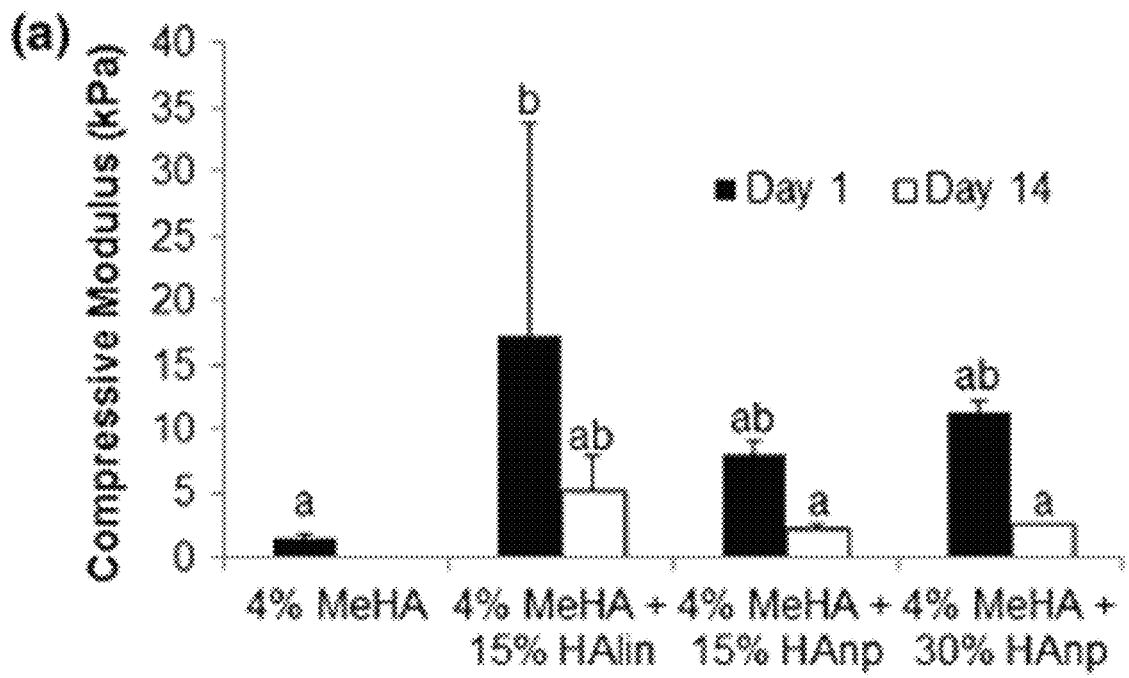
FIG. 3A includes a graph that shows the compressive modulus for different compositions at day 1 and day 14.
Figure 3B:
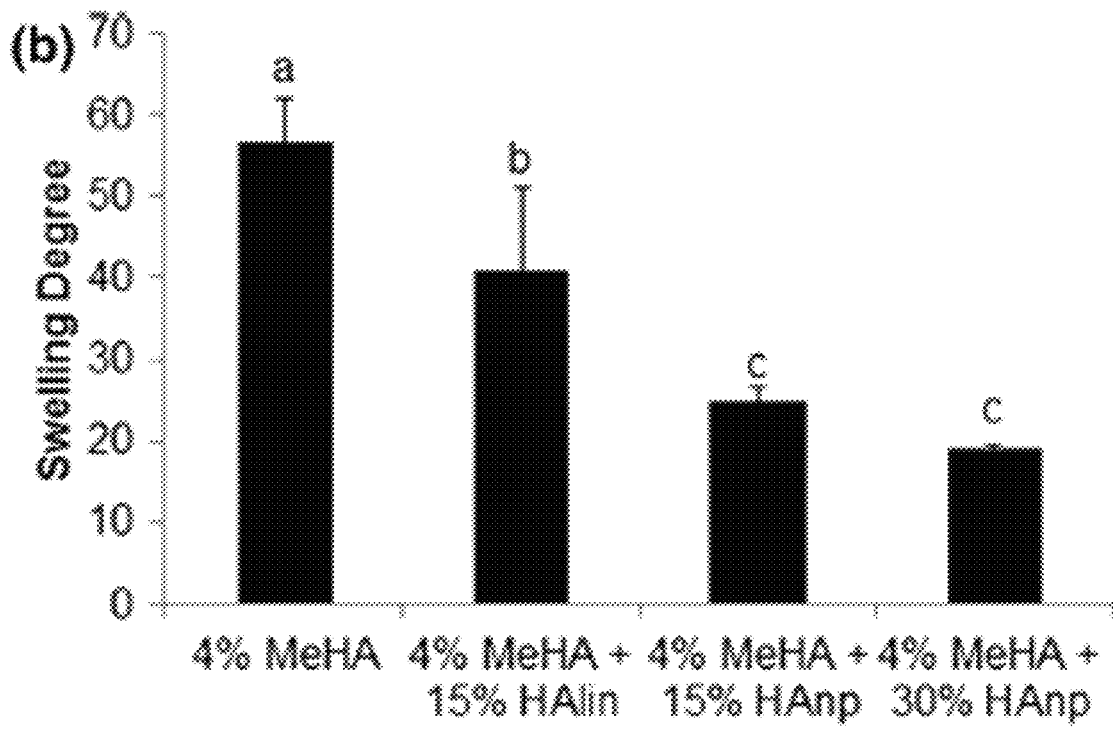
FIG. 3B includes a graph that shows the swelling degree for different compositions.

After characterizing the rheological behavior of the hydrogel precursor composition prior to crosslinking, the crosslinkable polymers were crosslinked with ultraviolet (UV) light and further characterized as solids. Preliminary tests revealed that crosslinked MeHA obtained gels with stable integrity over time in a 37° C. saline environment, therefore only gels containing MeHA were characterized after crosslinking. It should first be noted that gels containing 4% MeHA and either 15% HAlin or 30% HAlin were tested to compare with the hydrogel precursor compositions having HAnp, however, the mixtures containing 30% HAlin remained as solutions after crosslinking, rendering it impossible to cut gels for further testing, so the 30% HAlin mixtures were therefore discarded from further analysis. The addition of HAnp resulted in at least a fivefold increase in the compressive modulus compared to 4% MeHA hydrogels. The addition of HAnp significantly decreased the swelling degree after 1 day of swelling from 57 for 4% MeHA gels to 25 and 19 with the addition of 15% HAnp and 30% HAnp, respectively (see FIGS. 3A and 3B). FIG. 3A includes a graph that shows the compressive modulus for different compositions at day 1 and day 14. FIG. 3B includes a graph that shows the swelling degree for different compositions. After 14 days of swelling, the compressive moduli of the MeHA+HAnp gels decreased to a range where they were not significantly different from that of 4% MeHA gels after 1 day of swelling.

In one embodiment, the crosslinked hydrogel having the particles can have a compressive modulus of about 4 kPa to about 10 kPa, or from about 6.4 kPa to about 9.4 kPa, or from about 6.4 kPa to about 9.4 kPa, or a maximum compressive modulus of 10 kPa or a minimum compressive modulus of 4 kPa, or preferred compressive modulus of 8 kPa.

In one embodiment, the crosslinked hydrogel having the particles can have a swelling degree of about 20% to about 30%, or from about 23% to about 28%, or from about 24% to about 26%, or a maximum swelling degree of 30% or a minimum swelling degree of 20%, or preferred swelling degree of 25%.

Figure 4A:
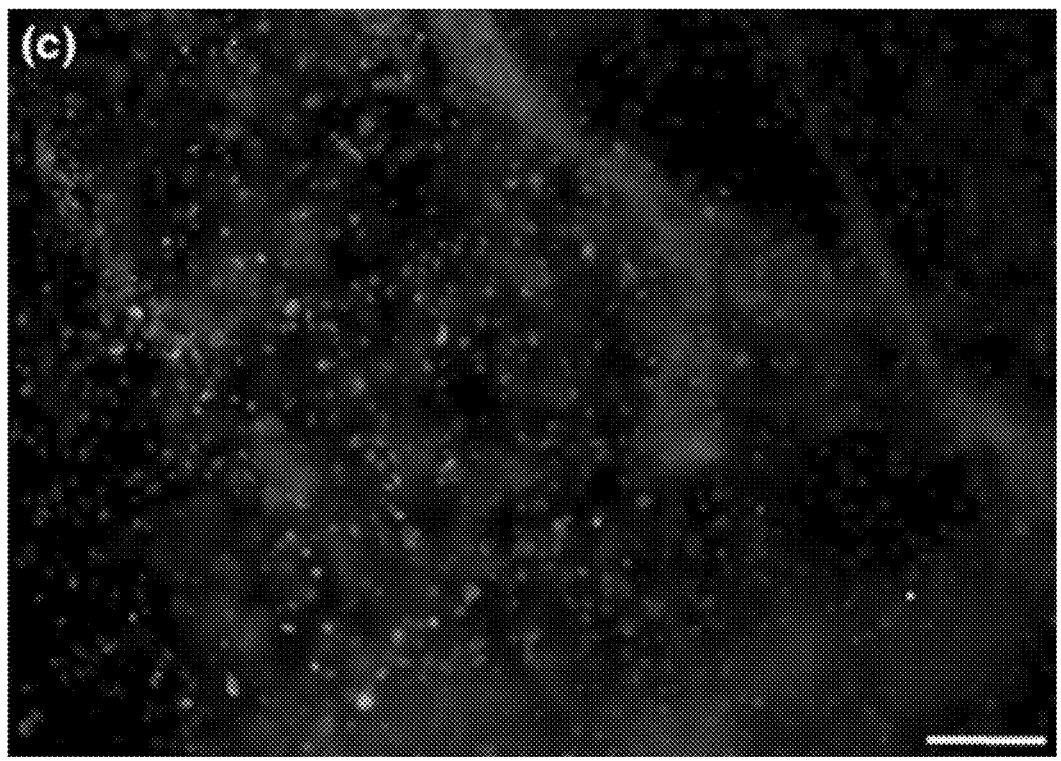
FIG. 4A includes an image that shows a hydrogel with 4% MeHA with few dead cells.
Figure 4B:
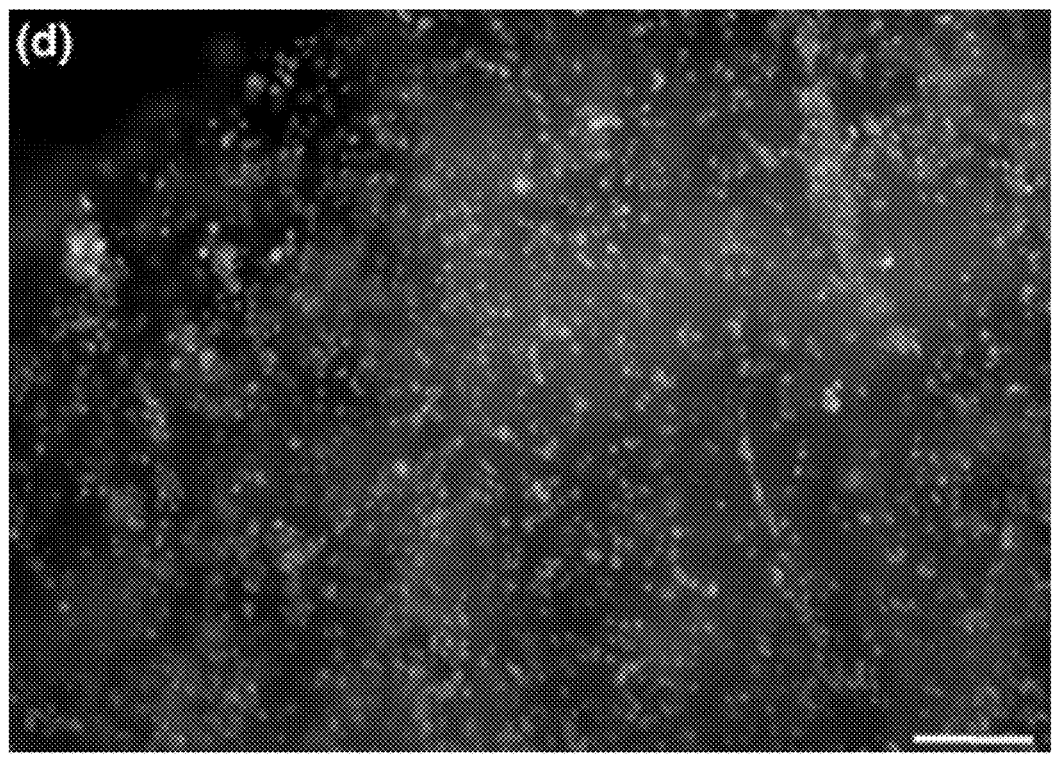
FIG. 4B includes an image that shows a hydrogel with 4% MeHA and 15% HAnp with few dead cells.

It was also found that after 4 weeks, rBMSCs (e.g., cells) encapsulated in the MeHA and MeHA+HAnp networks were viable as indicated by green fluorescence and minimal cell death (i.e., red fluorescence) was observed (e.g., FIGS. 4A and 4B with scale bars being 100 microns). FIG. 4A includes an image that shows a hydrogel with 4% MeHA with few dead cells. FIG. 4B includes an image that shows a hydrogel with 4% MeHA and 15% HAnp with few dead cells.

The benefits described herein with the use of the HAnp in the MeHA matrix in the hydrogel precursor forms a suitable composition with paste-like properties is thought to be from dangling HA chains on the surface of the HAnp providing interactions with the MeHA. These dangling chains are thought to cause physical entanglements between individual HAnp and entanglements between HAnp and MeHA. The desired paste-like behavior is attributed to the yield stress. The yield stress denotes the threshold where the composition transitions between an elastic solid and a pseudoplastic liquid, and it is desirable because it will prevent the hydrogel precursor from flowing away from a defect site of implantation. In a surgical context, this translates to allowing appropriate shaping and contouring the hydrogel precursor to the defect site. In one example, the hydrogel precursor can have yield stresses over 700 Pa to allow for molding, contouring and shaping prior to crosslinking. For context, the yield stresses for common paste-like materials, such as toothpaste, are approximately 200 Pa, and it can be beneficial for the hydrogel precursor to have a yield stress of or about 200 Pa. Because the only crosslinkable compositions exhibiting a yield stress incorporated HAnp, the yield stress was attributed to the HA being in the nanoparticle form, as the addition of linear HA (e.g., same MW but was linear instead of in nanoparticle form) was insufficient for achieving a yield stress. Furthermore, the combination of 4% MeHA with 15% HAnp produced a synergistic effect upon the yield stress. It should be noted that the 4% MeHA with 15% HAnp composition is a 19% overall concentration compared to the 15% HAnp composition, but this small increase in concentration is not assumed to account for the 3.4-fold increase in yield stress when 4% MeHA and 15% HAnp were combined. A lower molecular weight MeHA (e.g., 16 kDa) did not result in this synergistic effect seen with the 1 MDa MeHA, suggesting the synergistic effect is at least partially dependent on molecular weight of the crosslinkable polymer. Results suggest a desirable yield stress can be obtained for various applications by modulating the concentration of HAnp and the concentration and molecular weight of MeHA. The particle size of the HAnp may also be modulated for optimization and obtaining desired yield stress.

In addition to exhibiting a yield stress, it is desirable for hydrogel precursor to be able to recover rapidly after shearing. All samples containing HAnp recovered their original storage moduli within 5 minutes of disruption. Additionally, in contrast to the yield stress, which was dependent upon the presence of MeHA and concentration of HAnp, the storage modulus was dependent on the concentration of HAnp, regardless of the presence of MeHA. Overall, because HAnp gels exhibit a yield stress and recover rapidly, including HAnp in a polymer matrix of a hydrogel precursor may allow for precise molding without the risk of hydrogel precursor material leaking from an implantation site, making these hydrogel precursors suitable for a variety of topical and minimally invasive applications. After appropriate shaping and contouring of these hydrogel precursors pastes, it is also beneficial for the pastes to set up to form a rigid hydrogel network after crosslinking. Although the HAnp-incorporated hydrogel precursors exhibited the desirable yield stress and recovery after shearing, HAnp networks alone disintegrated rapidly in solution without the addition of MeHA. It is also noted that the 4% MeHA hydrogels without HAnp were disintegrated at 2 weeks, while the presence of HAnp kept the hydrogels intact. In these particular hydrogels, the HAnp are only physically entrapped in the system, so it is possible that chemically crosslinking the HAnp into the system may preserve and increase the mechanical properties if desirable. Thus, the HAnp may include cross-linkable functional groups, such as by being methacrylated (e.g., MeHAnp) particles. Furthermore, although the HAnp network may be short lived in the hydrogel, the addition of HAnp into traditional hydrogel precursor allow for the precursor solution to achieve paste-like rheological behavior, which is useful up until the point of crosslinking to form a shape-stable hydrogel. Additionally, rBMSCs encapsulated in these HAnp networks were viable at 4 weeks, which suggests that minimal cytotoxicity is feasible for HAnp-incorporated networks.

Stable hydrogels (e.g., defined as hydrogels that retained integrity for at least 6 weeks) were formed at a minimum ratio of 50:50 MeHA:HAnp by weight, at which point decreasing MeHA content resulted in a hydrogel that disintegrated before 6 weeks. Additionally, the 50:50 ratio only formed a stable gel at 30% minimum concentration of total concentration at w/v. Thus, 30% gels (w/v) at 100:0, 75:25, and 50:50 ratios were further analyzed. Here, the sum of the ratio adds up to 30% w/v overall. For example the 50:50 ratio contained 15% MeHA w/v and 15% HAnp w/v to add up to 30% w/v overall.

Figure 5:
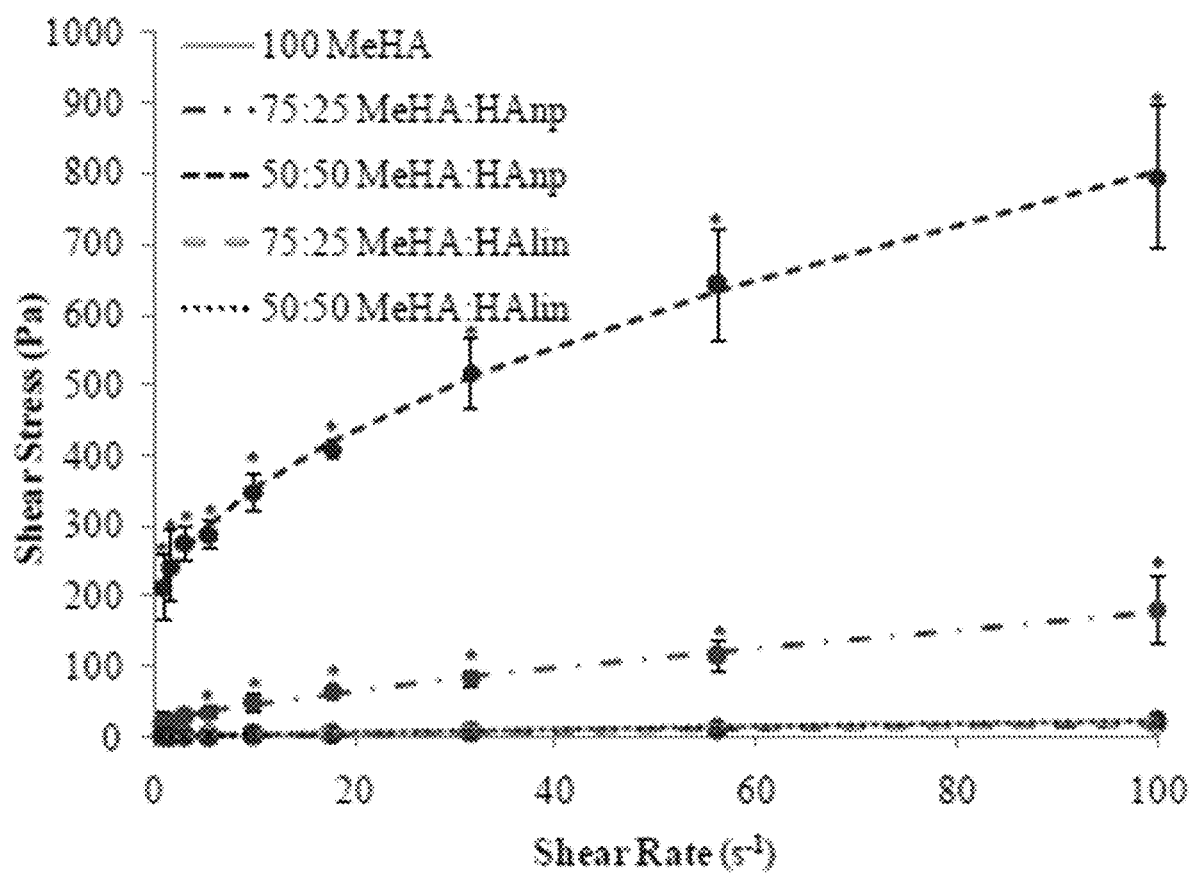
FIG. 5 includes a graph that shows increasing HAnp concentration increases yield stress.

Results showed that solutions containing HAnp exhibited H-B fluid behavior (see FIG. 5), as compared to the pure MeHA solution, which exhibited the Newtonian linear shear stress to shear rate relationship ($\tau 0=0$). FIG. 5 includes a graph that shows increasing HAnp concentration increases yield stress. The yield stresses observed in these gels are likely due to physical entanglements between individual HAnp and entanglements between HAnp and MeHA. The HAlin solutions at the same concentration of HAnp were also Newtonian. Therefore, H-B non-Newtonian behavior was attributed to the HAnp and not just the addition of exogenous HA. By fitting the HAnp solution data to the H-B equation, the yield stresses for the 75:25 and 50:50 MeHA:HAnp ratios were determined to be 18.5±3.7 Pa and 161.3±10.0 Pa (mean±SE), respectively. The swelling degree (Q) values for all gel ratios were found to range between 12.4 and 19.3 and no statistical significance was found, which suggests that incorporating HAnp does not affect gel swelling.

The elastic moduli of the hydrogel compositions are reported in Table 1. Decreasing MeHA content resulted in significantly lower moduli. Because the mechanical properties of MeHA hydrogels are attributed to crosslinking density, it is not surprising that decreasing MeHA concentration lowers the elastic moduli. Furthermore, the type of exogenous HA (i.e. HAnp versus HAlin) had no significant effect on mechanical properties.

TABLE 1

Elastic Moduli (E) of Gel Formulations

| Gel Formulation | E (kPa) |
| --- | --- |
| 100 MeHA | 239.8 ± 15.0 |
| 75:25 MeHA:HAnp | 146.8 ± 24.7 |
| 50:50 MeHA:HAnp | 42.5 ± 11.2 |
| 75:25 MeHA:HAlin | 127.5 ± 15.1 |
| 50:50 MeHA:HAlin | 36.1 ± 9.3 |

Referring to FIG. 5, the absorbance values for the control and cells exposed to HAnp and HAlin were 1.51±0.06, 1.20±0.05, and 1.30±0.03, respectively. The absorbance value of the control was significantly higher than the values from HAnp and HAlin exposure. Additionally, wells containing HAnp had a significantly lower absorbance value than those containing HAlin. However, observation at 100× magnification suggested the cells exposed to both forms of HA were healthy. Thus, lower absorbance values for HA exposure may be attributed to the cells differentiating (as opposed to dividing) and not necessarily due to cytotoxicity.

In one embodiment, a method of nerve regeneration can include preparing a hydrogel precursor composition having a crosslinkable polymer containing a polymer particle. The method can include introducing the hydrogel precursor composition into a body region in need of nerve regeneration, and crosslinking the crosslinkable polymer so as to contain the polymer particles therein and form a hydrogel.

In one embodiment, a method of cartilage regeneration can include preparing a hydrogel precursor composition having a crosslinkable polymer containing a polymer particle. The method can include introducing the hydrogel precursor composition into a body region in need of nerve regeneration such as a defective cartilage having a defect, and crosslinking the crosslinkable polymer so as to contain the polymer particles therein and form a hydrogel in the defect.

In one embodiment, a method of bone regeneration can include preparing a hydrogel precursor composition having a crosslinkable polymer containing a polymer particle. The method can include introducing the hydrogel precursor composition into a body region in need of nerve regeneration such as a defective bone having a defect, and crosslinking the crosslinkable polymer so as to contain the polymer particles therein and form a hydrogel in the defect.

In one embodiment, the cross-linkable polymer can include collagen, hyaluronate, chitosan, gelatin, algenate, pectin, carrageenen, chondroiten sulfate, dextran sulfate, polylysine, carboxymethyl chitin, fibrin, dextran, agarose, or pullulan or other natural polymer. These cross-linkable polymers can be used in place of or in addition to the hyaluronic acid polymer.

In one embodiment, the cross-linkable polymer can include synthetic polymers that include, poly(2-hydroxyethylmethacrylate (HE MA), polyphazene, poly(ethylene oxide) PEO and its copolymers, polyesters such as PEG (polyethylene giycol)-PLA (polylactic acid)-PEG, PEG-PLGA-PEG, PEG-PCL (poiycaprolactone)-PEG, PLA-PEG-PLA, PHB (poly(3-hydroxybutyrate)), P(PF-co-EG) plus or minus acrylate end groups, P(PER/PBO terephthaiate), other polymers such as PEG-bis-PLA-acrylate), PEG-g-P(Aam-co-Vamine), PAAm, P(NIPAAm-co-Aac), P(NIPAAm-co-EMA), PVAc PVA, PNVP, P(MMA-co-HEMA), P(AN-co-allyl sulfonate), P(biscarboxy-phenoxy-phosphazine), P(GEMA-suifate). These cross-linkable polymers can be used in place of or in addition to the hyaluronic acid polymer.

In one embodiment, the crosslinked hydrogels may be prepared from both natural and synthetic polymers, examples of which include P(PEG-co-peptides), alginate-g-(PEO-PPO-PEO), P(PLGA-co-serine), coliagen-acrylate, alginate-acrylate, P(HPMA-g-peptide), P(hema/Matrigel®), and HA-g-NIPAAm. In some embodiments, the hydrogel comprises a polymerized polyalkyleneglycolyl diacrylate. In another embodiment, the hydrogel comprises polyalkyleneglycolyl monoacrylates, including methacrylates. In yet another embodiment, the hydrogel comprises hyaluronic acid, chitosan, agarose, polyvinylacetate, polyvinylpyrrolide, or polyvinylalcohol nanoparticles.

In one embodiment, the particles can include PLG or PLGA particles. However the particles can be prepared from substantially any polymer, such as biocompatible, bioerodable, and/or biodegradable polymers. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, poly anhydrides, polyanhydride-co-imides, polyesters, polyorthoesters, polycaprolactones, polyesters, poly anhydrides, polyphosphazenes, poly(phosphoesters), polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinyl alcohol copolymers, polyvinylpyrrolidone (PVP), poly(L-lysine), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly(carboxyphenoxy hexane), poly(anhydride-co-imides), poly(amides), poly(iminocarbonates), poly(urethanes), poly(organophasphazenes), polyphosphates, poly(ethylene vinyl acetate) and other acyl substituted cellulose acetates and derivatives thereof, poly(amino acids), poly(acrylates), polyacetals, poly(cyanoacrylates), poly(styrenes), poly(vinyl chloride), poly(vinyl fluoride), polyvinyl imidazole), chlorosulfonated polyolefins, polyethylene oxide, combinations thereof, polymers having monomers thereof, or the like. In certain aspects, the particles may include hydroxypropyl cellulose (HPC), N-isopropylacrylamide (NIPA), polyethylene glycol, polyvinyl alcohol (PVA), polyethylenimine, chitosan, chitin, dextran sulfate, heparin, chondroitin sulfate, gelatin, etc. and their derivatives, co-polymers, and mixtures thereof. These particles can be used in place of or in addition to the hyaluronic acid polymer particles.

In one embodiment, the hydrogel precursor and resulting crosslinked hydrogel can include one or more therapeutic agents that are useful in tissue engineering scaffold applications. The incorporated references include lists of such agents.

In one embodiment, the present invention provides a method of treating an osteochondral defect, which method comprises the step of contacting an osteochondral defect with a hydrogel precursor composition and crosslinking the hydrogel precursor composition into a hydrogel in the defect. Osteochondral defects are joint disorders in which lesions form in the articular cartilage and the underlying subchondral bone. Osteochondral defects are common in humans, as well as in other animals including horses. Osteochondral defects most commonly affect knee, and other joints such as in children. As provided in this method, said osteochondral defects include those that occur, whether caused by traumatic injury or osteoarthritis, in knees, ankles, elbows, patellas, vertebrae, femoral heads, glenoids of the scapula, and growth plates, which may be treated by repairing cartilage. The hydrogel precursor compositions can conveniently be placed into, for example, holes, gaps, or spaces of any shape in tissues and organs so as to substantially fill such holes, gaps, or spaces. In one embodiment, such holes, or gaps or spaces, are cartilage lesions in various osteochondral defects.

Additionally, the hydrogel precursor compositions can be used in a method of treating full and partial thickness cartilage defects by applying the hydrogel precursor therein and then crosslinking in the defect. In humans, when articular cartilage fails to heal spontaneously, it leads to partial-thickness cartilage lesions that have fissures less than 1.5 cm in diameter. The exposed cell surfaces in the lesion cannot support cell adhesion, cell migration or fibrin clot attachment. When the fissures extend down to subchondral bone and have diameter greater than 1.5 cm, it is often categorized as full-thickness cartilage lesions. Full or partial thickness cartilage defects can affect any cartilaginous structure including the knee, elbow, wrist, ankle, shoulder and hip joints. Therefore, the method of treating partial-thickness cartilage lesions includes treating any cartilage defect including those selected from the group of knee, elbow, wrist, ankle, shoulder and hip joints.

EXAMPLES

Synthesis of methacrylated HA (MeHA) and HAnp was performed. MeHA was prepared by reacting HA (MW 16 kDa and 1 MDa) with 20-fold molar excess glycidyl methacrylate (e.g., 20 mol glycidyl methacrylate per 1 mol HA monomer) in the presence of 20-fold molar excess trimethylamine and tetrabutyl ammonium bromide for 12 days stirring in a 50:50 water:acetone solution at 200 rpm. MeHA was then dialyzed against deionized (DI) water for 2 days and was then frozen and lyophilized. The degree of methacrylation was analyzed by calculating the ratio of the relative peak area of methacrylate protons to methyl protons.

HAnp were prepared using carbodiimide crosslinking chemistry using EDC with adipic acid dihydrazide (AAD) as the crosslinker. Briefly, 300 mg HA (16 kDa) was dissolved in 120 mL DI water in a 500 mL round flask stirring at 300 rpm. Then, 200 mL acetone was added to the flask and stirred for 15 min. AAD (60 mg) was dissolved in 1 mL DI water and added to the flask for 10 min. Similarly, 140 mg EDC was dissolved in 1 mL DI water and added to the flask for 20 min. Another 200 mL acetone was then added to the flask and the reaction was allowed to stir for 3 h. The solution was then dialyzed against DI water for 2 days and the particles were frozen and lyophilized. Repeated batches of HAnp were fabricated in this manner and combined for later testing. Particle size was measured using a ZetaPALS dynamic light scattering instrument (Brookhaven, USA). Particle morphology was examined with scanning transmission electron microscopy (STEM) images.

The hydrogel precursor compositions were made by mixing varying weight percent of HA (i.e., MeHA and HAnp) in 0.01 M phosphate buffered saline (PBS) containing 0.05% (w/v) Irgacure (1-2959) photoinitiator (e.g., 15% HAnp=15 mg HAnp in 100 1 L PBS). Linear HA (HAlin) at 16 kDa (i.e., the same molecular weight used to make the HAnp) was also mixed with MeHA as a control to discern whether yield stress differences were due to the HA being in the nanoparticulate form or due to the mere addition of extra HA.

Also, to determine a leading MeHA:HAnp ratio and overall weight percent, gels (n=1) were fabricated at 15%, 20%, 25%, 30%, and 35% (w/v) at ratios of 100:0, 75:25, 50:50, 25:75, and 0:100 (MeHA:HAnp). The gels were swollen in PBS for up to 6 weeks and the integrity of the gels were recorded weekly.

Prior to crosslinking the hydrogels, the shear stress of the hydrogel precursor compositions (n=5) were measured over a shear rate sweep of 0.01-100 $s^{-1}$ at 37° C. Preliminary work suggested that a 15% HAnp solution was sufficient to obtain a yield stress, and 4% MeHA was chosen because it was at the reconstitution limit of MeHA. Formulations tested were 4% MeHA, 15% HAlin, 4% MeHA+15% HAlin, 30% HAlin, 4% MeHA+30% HAlin, 15% HAnp, 4% MeHA+15% HAnp, 30% HAnp, and 4% MeHA+30% HAnp. The yield stresses of solutions were calculated using a three parameter fitting technique to fit the data to the Herschel-Bulkley equation (Eq. 1), where $\tau$ is the shear stress, $\tau_0$ is the yield stress, $\kappa$ is the consistency index, $\gamma$ is the shear rate, and n is the flow behavior index.

Gels (n=5) at 30% w/v and at ratios of 100:0, 75:25, and 50:50 (MeHA:HAnp and MeHA:HAlin) were swollen in PBS for 24 hours and then weighed. The dry weight was recorded after lyophilization and the swelling ratio (Q) was calculated as the ratio of total wet mass to dry mass.

Oscillatory tests were performed first by doing a stress sweep at 1 Hz to determine the linear iscoelastic region of the solutions. Solutions (n=5) were then exposed to three phases of oscillatory shearing at 1 Hz: 5 min at a constant shear stress of 10 Pa (i.e., within the linear viscoelastic region of the pseudoplastic solutions), a disruption phase lasting 30 s at a constant shear stress of 1000 Pa (i.e., sheared above the yield stress), and another 5 min at a constant shear stress of 10 Pa.

The gels were compressed at a rate of 0.005 mm/s until mechanical failure and the elastic modulus was calculated as the slope under the linear portion of the stress-strain curve (n=6).

Gel compositions of experimental groups containing 4% MeHA were placed in a 2 mm thick mold between glass slides and exposed to 312 nm UV light at 3.0 mW/cm² for 15 min on each side. Gels were cut using a 3 mm biopsy punch. To calculate the swelling degree, gels were swollen in PBS for 24 h and then weighed and lyophilized (n=6). The dry weight was recorded after lyophilization and the swelling ratio (Q) was calculated as the ratio of total wet mass to dry mass. To obtain the compressive modulus, gels were swollen in PBS for 24 h or 2 weeks (n=6) and were compressed at a rate of 0.005 mm/s until mechanical failure and the elastic modulus was calculated as the slope under the linear portion of the stress-strain curve.

Rat bone marrow-derived mesenchymal stem cells (rBMSCs) were harvested from the femurs of male Sprague-Dawley rats (200-250 g). The rBMSCs were cultured in monolayer until passage four for cell seeding. Media consisted of low glucose Dulbecco's Modified Eagle's Medium, 10% Qualified Fetal Bovine Serum, 1% Antibiotic-Antimycotic and was replaced every other day throughout culture. For encapsulation, cells were suspended in the photoinitiator solution at a cell density of 10 million cells and then mixed with either 4% MeHA or 4% MeHA+15% HAnp. Hydrogels were then fabricated using the same previously described technique to make acellular gels. After 4 weeks of culture, the gels were stained with live/dead reagent (2 mM calcein AM, 4 mM thidium homo-dimer-1; Molecular Probes), incubated for 20 min, and then analyzed using fluorescence microscopy. However, any other cells may be included in the hydrogel precursor and then encapsulated by crosslinking into the hydrogel.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety: WO 2013/109959 and WO 2015/048317.

The invention claimed is:

1. A method of forming a hydrogel implant, comprising:
providing an implantable hydrogel precursor composition that has a yield stress at zero shear rate, the implantable hydrogel precursor composition comprising:
 a cross-linkable polymer matrix that is biocompatible, wherein the cross-linkable polymer matrix includes a cross-linkable hyaluronic acid polymer that has cross-linkable functional groups; and
 a plurality of polymer particles in the cross-linkable polymer matrix, the polymer particles include a cross-linked hyaluronic acid;
implanting the hydrogel precursor composition into a body of a subject such that the hydrogel precursor composition has a shape and shape retention while in the body; and
crosslinking the cross-linkable polymer matrix to form a hydrogel containing the plurality of polymer particles that has the shape.

2. The method of claim 1, further comprising shaping the hydrogel precursor composition to have the shape with shape retention while in the body.

3. The method of claim 2, further comprising:
placing the hydrogel precursor in a defect in a tissue in the body; and
crosslinking the cross-linkable polymer in the defect.

4. The method of claim 3, wherein while in the defect, the hydrogel precursor composition retains the shape without leaking or flowing out of the defect.

5. The method of claim 2, further comprising shaping the hydrogel precursor composition with an instrument to obtain the shape.

6. The method of claim 3, wherein the defect is in a cartilage tissue, a bone tissue, or a nerve tissue.

7. The method of claim 1, further comprising:
placing cells within the hydrogel precursor composition; and
performing the crosslinking with the cells within the cross-linking composition.

8. The method of claim 1, further comprising:
providing a cross-linkable polymer matrix that is biocompatible; and
mixing a plurality of polymer particles into the cross-linkable polymer matrix.

9. The method of claim 3, further comprising forming the defect in the tissue.

10. The method of claim 8, further comprising:
providing a bioactive agent; and
mixing the bioactive agent into the cross-linkable polymer matrix.

11. The method of claim 1, further comprising:
regenerating bone with the hydrogel;
regenerating cartilage with the hydrogel; or
regenerating nerves with the hydrogel.

12. The method of claim 11, further comprising treating a full or partial thickness cartilage defect with the hydrogel.

13. The method of claim 1, wherein the hyaluronic acid polymer is a methacrylated hyaluronic acid polymer.

14. The method of claim 13, wherein the methacrylated hyaluronic acid polymer has a molecular weight from about 500 kDa to about 1.8 MDa.

15. The method of claim 1, wherein the hyaluronic acid polymer particles have a molecular weight of about 10 kDa to about 20 kDa.

16. The method of claim 1, wherein the implantable hydrogel precursor composition comprises:
the cross-linkable hyaluronic acid polymer is present from about 2% to about 10%; and
the polymer nanoparticles are present from about 10% to about 40%.

17. The method of claim 16, wherein:
the polymer nanoparticles have a molecular weight of about 10 kDa to about 20 kDa;
the polymer nanoparticles have a particle size of about 10 nm to about 500 nm; and
a ratio of cross-linkable hyaluronic acid polymer to polymer nanoparticles is from 1:15 to about 2:1.

18. The method of claim 16, wherein the implantable hydrogel precursor composition comprises:
live cells; and/or
a biologically active agent.

19. The method of claim 16, wherein the implantable hydrogel precursor composition comprises:
a non-zero shear stress at a shear rate below 1 s-1;
a shear stress of about 500 Pa to about 1000 Pa at 1 s-1 shear rate;
a yield stress of at least about 400 Pa to about 800 Pa; and/or
a storage modulus: about 400 Pa to about 1100 Pa at an initial phase, about 10 Pa to about 400 Pa at a disruption phase, and about 500 Pa to about 1200 Pa at a recovery phase.

* * * * *